United States Patent
Geysen

(10) Patent No.: US 9,273,092 B2
(45) Date of Patent: Mar. 1, 2016

(54) SELECTIVE BINDING COMPOUNDS

(71) Applicant: RIOGIN Corporation, Charlottesville, VA (US)

(72) Inventor: Hendrik Mario Geysen, Charlottesville, VA (US)

(73) Assignee: RioGin LLC, Charlottesville, VA (US)

( * ) Notice: Subject to any disclaimer, the term of this patent is extended or adjusted under 35 U.S.C. 154(b) by 0 days.

(21) Appl. No.: 13/726,112

(22) Filed: Dec. 22, 2012

(65) Prior Publication Data

US 2013/0165624 A1  Jun. 27, 2013

Related U.S. Application Data

(60) Provisional application No. 61/579,823, filed on Dec. 23, 2011, provisional application No. 61/651,516, filed on May 24, 2012.

(51) Int. Cl.
| | |
|---|---|
| *C07K 1/107* | (2006.01) |
| *C07K 7/06* | (2006.01) |
| *C07K 7/08* | (2006.01) |
| *A61K 47/48* | (2006.01) |

(52) U.S. Cl.
CPC ............ *C07K 7/06* (2013.01); *A61K 47/48246* (2013.01); *C07K 1/1075* (2013.01)

(58) Field of Classification Search
CPC ... A61K 47/48246; C07K 1/1075; C07K 7/06
See application file for complete search history.

(56) References Cited

U.S. PATENT DOCUMENTS

| 6,348,568 B1 * | 2/2002 | Barney et al. ............... 530/300 |
| 2005/0187139 A1 | 8/2005 | Assaly et al. |
| 2007/0105750 A1 | 5/2007 | Dorwald et al. |
| 2009/0111745 A1 | 4/2009 | Tomlinson |
| 2010/0172844 A1 | 7/2010 | Neri et al. |
| 2011/0059076 A1 | 3/2011 | McDonagh et al. |

FOREIGN PATENT DOCUMENTS

| EP | 1581583 B1 | 3/2010 |
| WO | 2005027978 A2 | 3/2005 |
| WO | 2011021014 A2 | 2/2011 |
| WO | 2011106639 A1 | 9/2011 |

OTHER PUBLICATIONS

Dennis et al., Albumin Binding as a General Strategy for Improving the Pharmacokinetics of Proteins, Journal of Biological Chemistry, vol. 277(38):35035-35043 (Sep. 20, 2002).*
NCBI.NLM.NIH.gov, GenBank: AAO32799.1, (Jun. 2, 2003) attached as pdf, also available at http://www.ncbi.nlm.nih.gov/protein/AAO32799, last visited Jun. 19, 2014.*
NCBI.NLM.NIH.gov, GenBank:AB013696, (Sep. 28, 2000) attached as pdf, also available at http://www.ncbi.nlm.nih.gov/nuccore/AB013696, last visited Jun. 19, 2014.*
NCBI.NLM.NIH.gov, GenBank: AAH61285.1 (Jul. 15, 2006), attached as pdf, also available at http://www.ncbi.nlm.nih.gov/protein/AAH61285.1, last visited Jun. 19, 2014.*
Kratz, "Albumin as a Drug Carrier: Design of Prodrugs, Drug Conjugates and Nanoparticles," Journal of Controlled Release 132(3):171-183 (2008).
Schmid et al., "Albumin-Binding Prodrugs of Camptothecin and Doxorubicin with an Ala-Leu-Ala-Leu-Linker that are Cleaved by Cathepsin B: Synthesis and Antitumor Efficacy," Bioconjugate Chem. 18(3):702-716 (2007).

* cited by examiner

*Primary Examiner* — James H Alstrum Acevedo
*Assistant Examiner* — Randall L Beane
(74) *Attorney, Agent, or Firm* — LeClairRyan; Jeffrey N. Townes

(57) ABSTRACT

Compounds which can include an active (drug) moiety have the general formula (I):

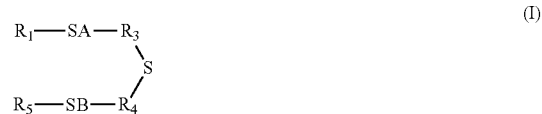

wherein: SA is a pentapeptide aa1-aa2-aa3-aa4-aa5, wherein at least one of aa1, aa2, aa3, aa4, and aa5 is L, I, E, D, and I, respectively, wherein L, I, E, and D are eponymous amino acids; SB is a dipeptide aa6-aa7, wherein at least one of aa6 and aa7 is L and W, respectively, wherein W and L are eponymous amino acids; $R_1$ and $R_5$ are N-, and C-terminal moieties, respectively; $R_3$ and $R_4$ are independently a linker selected from a substituted or unsubstituted methylene, an amino acid, a peptide, and a peptide bond; and S is a scaffold moiety, a bond, a peptide bond, an amino acid, or a peptide of up to three residues, wherein $R_3$, S, and $R_4$ together form a turn in the compound, and the compound selectively binds a serum albumin.

4 Claims, No Drawings

SELECTIVE BINDING COMPOUNDS

CROSS REFERENCE TO RELATED APPLICATIONS

This application claims priority under 35 U.S.C. §119(e)(1) to No. 61/579,823, filed Dec. 23, 2011, and No. 61/651,516, filed May 24, 2012, the disclosures of which are incorporated herein by reference in their entireties.

INTRODUCTION

We have developed compounds that selectively bind a serum albumin. The compounds contain a turn in the primary or secondary structure, and in some embodiments can include an active (drug) moiety.

US 2010/0121039 describes peptide ligands having affinity for IgG or for serum albumin.

US 2011/0059076 describes a human serum albumin linker and HSA linker with binding, diagnostic, and therapeutic agents conjugated thereto.

SUMMARY OF THE INVENTION

In one aspect, the invention provides a compound of general formula (I):

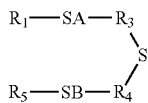
(I)

wherein:

SA is a pentapeptide aa1-aa2-aa3-aa4-aa5, wherein at least one of aa1, aa2, aa3, aa4, and aa5 is L, I, E, D, and I, respectively, wherein L, I, E, and D are eponymous amino acids;

SB is a dipeptide aa6-aa7 (wherein aa6 connects to R4 and aa7 connects to R5, wherein at least one of aa6 and aa7 is L and W, respectively, wherein L and W are eponymous amino acids;

R1 and R5 are N-, and C-terminal moieties, respectively;

R3 and R4 are independently a linker selected from a substituted or unsubstituted methylene, an amino acid, a peptide, a bond, and a peptide bond; and S is a scaffold moiety, a bond, a peptide bond, an amino acid, or a peptide of up to three residues, wherein R3, S, and R4 together form a turn in the compound, and the compound selectively binds a serum albumin.

In various embodiments:

two of aa1, aa2, aa3, aa4, and aa5 are L, I, E, D, and I, respectively;

three of aa1, aa2, aa3, aa4, and aa5 are L, I, E, D, and I, respectively;

four of aa1, aa2, aa3, aa4, and aa5 are L, I, E, D, and I, respectively;

SA is LIEDI (SEQ ID NO: 1) and SB is LW;

S comprises fewer than 4 residues;

S, SA, SB, $R_3$, $R_4$, $R_1$, or $R_5$ is conjugated to a drug or label, optionally through a functional linking moiety;

S is conjugated to a drug selected from: Aviptadil, Bivalirudin, Calcitonin(human), Calcitonin(salmon), Carperitide, Desmopressinm, Enfurivirtide, Eptifibatide, Exenatide, Lanreotide, liraglutide, Mifamurtide, Nesirtide, Pramlintide, Romiplostim, Taltirelin, parathyroid hormone (PTH), glucagon-like peptide-1 (GLP-1), and Teriparatide, or a fragment thereof;

the compound has improved PK compared with the free drug;

$R_3$ and $R_4$ are peptides that bind each other though a moiety selected from a disulfide, an amide, an ether, a thioether, or a methylene;

$R_3$ and $R_4$ are cysteine residues that bind each other through disulfide binding;

S is proline, lysine, alanine, proline, glycine, a dipeptide, or a benzoic acid derivative;

S is selected from optionally substituted, optionally heteroatom-containing, cycloalkyl or aryl joining $R_3$ and $R_4$ though 3, 4, 5, 6, 7, 8, or 9 bonds;

$R_3$—S—$R_4$ comprises a structure selected from:

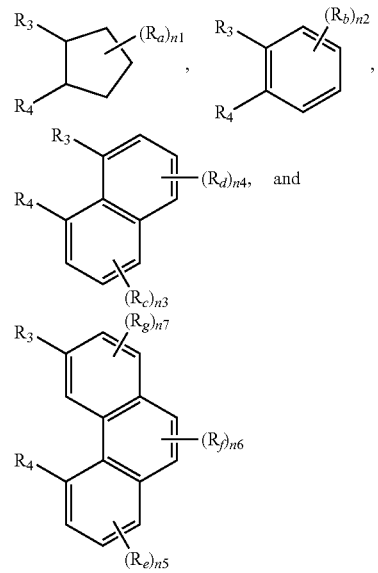

wherein: n1, n3, n4, n5, and n7 are integers selected from 0, 1, 2, and 3; n2 is an integer from 0 to 4; n6 is an integer selected from 0, 1, and 2; and Ra, Rb, Rc, Rd, Re, Rf, and Rg are substituents selected from optionally substituted and optionally heteroatom-containing alkyl or aryl, provided that any two adjacent substituents may be linked to form one or more rings;

$R_1$ is N—R, wherein N is a N-terminal moiety, and R is arginine or lysine, or wherein $R_1$ is acyl.

$R_1$ is acyl;

$R_5$ is amide;

$R_3$ and $R_4$ are separated by 1, 2, 3, 4, or 5 peptide bonds;

the serum albumin is human serum albumin.

In another aspect, the invention provides a method for modifying a drug to alter a pharmacokinetic property of the drug, the method comprising attaching or incorporating the drug into $R_1$, $R_3$, $R_4$, $R_5$, SA, SB, or S into a compound according to general formula (I).

In various embodiments:

the drug is conjugated to S, $R_1$, or $R_5$, optionally through a functional linking moiety; and the method improves the PK of the drug.

In another aspect, the invention provides a method for treating a patient comprising administering to the patient a compound according to general formula (I).

In another aspect, the invention provides a compound of the general formula (II):

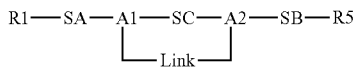

wherein:

SA, SB, R1, and R5 are as described for formula (I);

SC is a linker selected from a bond, a peptide bond, an amino acid, a di-peptide and a tri-peptide;

A1 and A2 are amino acids; and

Link is a bond between the side-chains of amino acids A1 and A2.

In various embodiments of formula (II):

two of aa1, aa2, aa3, aa4, and aa5 are L, I, E, D, and I, respectively;

three of aa1, aa2, aa3, aa4, and aa5 are L, I, E, D, and I, respectively;

four of aa1, aa2, aa3, aa4, and aa5 are L, I, E, D, and I, respectively;

SA is LIEDI (SEQ ID NO: 1) and SB is LW;

SA is LIEDI (SEQ ID NO: 1), SC is P and SB is LW;

A1 and A2 are Cysteine residues and Link is a disulfide Bond; and

Link is selected from a disulfide, an amide, an ether, a thiol ether, or a methylene linkage.

In another aspect, the invention provides a compound of the general formula (III)

wherein:

R1, SA, SB, and R5 are as defined for formula (II); and

Sca is a non-peptide chemical entity that connects SA to SB such that the shortest bond-path is n, where $2<n<10$ bonds.

The invention specifically provides all combinations of the recited aspects, as if each had been laboriously individually set forth.

DETAILED DESCRIPTION OF PARTICULAR EMBODIMENTS

In one aspect, the invention provides a compound of general formula (I):

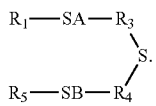

In formula (I), SA is a pentapeptide aa1-aa2-aa3-aa4-aa5, wherein at least one of aa1, aa2, aa3, aa4, and aa5 is L, I, E, D, and I, respectively, wherein L, I, E, and D are eponymous amino acids. In some embodiments, at least two of aa1, aa2, aa3, aa4, and aa5 is L, I, E, D, and I, respectively. In some embodiments, at least three of aa1, aa2, aa3, aa4, and aa5 is L, I, E, D, and I, respectively. In some embodiments, at least four of aa1, aa2, aa3, aa4, and aa5 is L, I, E, D, and I, respectively. In some embodiments, aa1, aa2, aa3, aa4, and aa5 are L, I, E, D, and I, respectively.

For example, SA can be:

L-aa2-aa3-aa4-aa5; aa1-I-aa3-aa4-aa5; aa1-aa2-E-aa4-aa5; aa1-aa2-aa3-D-aa5; aa1-aa2-aa3-aa4-I;

L-I-aa3-aa4-aa5; L-aa2-E-aa4-aa5; L-aa2-aa3-D-aa5; L-aa2-aa3-aa4-I; aa1-I-E-aa4-aa5; aa1-I-aa3-D-aa5; aa1-I-aa3-aa4-I; aa1-aa2-E-D-aa5; aa1-aa2-E-aa4-I; aa1-aa2-aa3-D-I;

L-I-E-aa4-aa5; L-I-aa3-D-aa5; L-I-aa3-aa4-I; L-aa2-E-D-aa5; L-aa2-E-aa4-I; L-aa2-aa3-D-I; aa1-I-E-D-aa5; aa1-I-E-aa4-I; aa1-I-aa3-D-I; aa1-aa2-E-D-I;

L--I--E--D--aa5 (SEQ ID NO: 2); L--I--E--aa4--I (SEQ ID NO: 3); L--I--aa3--D--I (SEQ ID NO: 4); L--aa2--E--D--I (SEQ ID NO: 5); aa1--I--E--D--I (SEQ ID NO: 6); or

L--I--E--D--I (SEQ ID NO: 1).

In formula (I), SB is a dipeptide aa6-aa7, wherein at least one of aa6 and aa7 is L and W, respectively, wherein W and L are eponymous amino acids. Thus, SB can be L-W, L-aa7, or aa6-W. SB connects to $R_4$ (or S, when $R_4$ is a bond) via aa6, and connects to $R_5$ via aa7.

The symbols aa1, aa2, aa3, aa4, aa5, aa6, and aa7 represent individual amino acids. These are selected from natural amino acids and non-natural amino acids.

In formula (I), $R_1$ is a N-terminal moiety. In some embodiments, $R_1$ includes one or more amino acids as well as a N-terminal moiety (in such embodiments, the whole of $R_1$ is still referred to as a N-terminal moiety). In some embodiments, $R_1$ includes linking moieties such as alkylene, arylene, alkarylene, aralkylene, and the like. In some embodiments, $R_1$ includes a terminal moiety selected from alkyl, aryl, alkaryl, aralkyl, and the like. In some embodiments, $R_1$ includes a functional group that may be a linking moiety or a terminal moiety as appropriate. Examples of functional groups include halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—(CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)2), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N+≡C—), cyanato (—O—C≡N), isocyanato (—O—N≡C—), isothiocyanato (—S—C≡N), azido (—N=N+=N—), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO2), nitroso (—NO), sulfo (—SO$_2$—OH), sulfonato (—SO$_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$s-$C_{20}$ arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$), mono- and di-($C_1$-$C_{24}$ alkyl)-substituted phosphino, and mono- and di-($C_5$-$C_{20}$ aryl)-substituted phosphino. In some embodiments, $R_1$ is an active moiety, or is conjugated to an active moiety, as explained in more detail below. A specific example of $R_1$ is acyl.

In formula (I), $R_5$ is a C-terminal moiety. In some embodiments, $R_5$ includes one or more amino acids as well as a C-terminal moiety (in such embodiments, the whole of $R_5$ is still referred to as a C-terminal moiety). In some embodiments, $R_5$ includes linking moieties such as those described for $R_1$. In some embodiments, $R_5$ includes a terminal moiety such as those described for $R_1$. In some embodiments, $R_5$ includes a functional group that may be a linking moiety or a terminal moiety as appropriate. Examples of functional groups include those provided for $R_1$. In some embodiments, $R_5$ is an active moiety, or is conjugated to an active moiety, as explained in more detail below. Specific examples of $R_5$ are amide, peptide, carboxylate group, amino acid, and H. The amide can be unsubstituted ($-NH_2$), monosubstituted ($-NHR_a$) or disubstituted ($-NR_aR_b$), wherein each instance of $R_a$ and $R_b$ are independently selected from alkyl, aryl, alkaryl, aralkyl, functional groups such as those provided for $R_1$, or the like.

In formula (I), $R_3$ and $R_4$ are independently a linker selected from a substituted or unsubstituted methylene, an amino acid, a peptide, and a peptide bond. As amino acids, $R_3$ and $R_4$ may be selected from any natural or non-natural amino acid. As peptides, $R_3$ and $R_4$ may be of any length (e.g., 1, 2, 3, 4, 5, or more than 5 amino acids) and may comprise natural amino acids, non-natural amino acids, or both. $R_3$ and/or $R_4$ may be unsubstituted methylene (i.e., $-CH_2-$), monosubstituted methylene (i.e., $-CHR_a-$), or disubstituted methylene (i.e., $-CR_aR_b-$), wherein each instance of $R_a$ and $R_b$ are independently selected from alkyl, aryl, alkaryl, aralkyl, functional groups such as those provided for $R_1$, or the like. Furthermore, $R_a$ and $R_b$ may be taken together to form a cyclic moiety (e.g., cycloalkyl) or as an oxygen atom (such that $R_3$ or $R_4$ is a carbonyl). $R_3$ attaches to SA via the N-terminus of SA, and $R_4$ attaches to SB via the C-terminus of SB. Some specific examples of $R_3$ and $R_4$ are methylene, cysteine, and the like.

In formula (I), S is a scaffold moiety, a bond, an amino acid, or a peptide sequence of up to three residues. In some embodiments, S is selected from a bond, a peptide bond, an amino acid, a peptide, and a scaffold moiety. As a peptide or amino acid, S is prepared from natural and/or non-natural amino acids. In such embodiments, $R_3$ and $R_4$ are separated by 1 or 2 peptide bonds (i.e., S is a peptide that provides such separation between $R_3$ and $R_4$). As a scaffold moiety, S is an organic moiety other than an amino acid or peptide. Further details for S are provided herein.

The combination of $R_3$, $R_4$, and S forms a turn in the compound. The type of turn will be determined by the identity of $R_3$, $R_4$, and S. For example, a β-turn is obtained by three peptide bonds, such as when $R_3$ and $R_4$ are each an amino acid and S is a peptide comprising two amino acids. Four peptide bonds typically provide an α-turn, two peptide bonds typically provide a γ-turn, five peptide bonds typically provide a π-turn, and one peptide bond typically provides a δ-turn (e.g., when $R_3$ and $R_4$ are each an amino acid and S is a bond).

The turn formed by $R_3$, $R_4$, and S may be the result of a bridge formed in a compound according to formula (I), such as when $R_3$ and $R_4$ are capable of forming a bridge. A bridge is a covalent linkage between the side chains of two amino acids (i.e., a linkage between the side chain of an amino acid in R3 with the side chain of an amino acid in R4). Examples of such linkages include the following moieties: a disulfide, an ether, an amide, a thiol ether, and an alkyl such as a methylene. For example, when $R_3$ and $R_4$ are both cysteine or are both serine, the compound can form a disulfide bond or an ether bond, respectively, that holds $R_3$, $R_4$, and S in the form of a turn. The combination of a serine (or a serine analog) and cysteine provides a thioether bond to form the turn. The combination of aspartic acid and ornithine can form an amide bond. These examples are not limiting, and other combinations for forming a bridge are possible.

Where S is a peptide, S comprises fewer than 4 residues, such as 3 or 2 residues. S may also be a single amino acid, such as lysine, alanine, proline, or glycine.

The turn formed by $R_3$, $R_4$, and S may be a feature of the structure of a compound according to formula (I), such as when S is a scaffold moiety. In some such embodiments, S is a cyclic moiety, and $R_3$ and $R_4$ are appropriately positioned substituents on S. The number of bonds separating $R_3$ from $R_4$ (i.e., the number of bonds separating the atom of $R_3$ connecting $R_3$ to S and the atom of $R_4$ connecting $R_4$ to S) is 3, 4, 5, 6, 7, 8, or 9.

For example, with S as a scaffold moiety, $R_3-S-R_4$ can have a structure selected from:

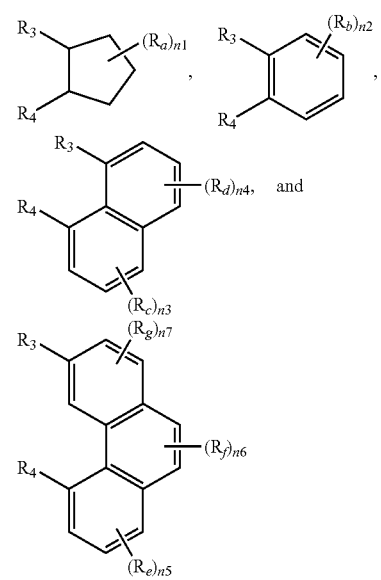

wherein: n1, n3, n4, n5, and n7 are integers selected from 0, 1, 2, and 3; n2 is an integer from 0 to 4; n6 is an integer selected from 0, 1, and 2; and Ra, Rb, Rc, Rd, Re, Rf, and Rg are substituents selected from optionally substituted and optionally heteroatom-containing alkyl or aryl, provided that any two adjacent substituents may be linked to form one or more rings. Any one of Ra, Rb, Rc, Rd, Re, Rf, or Rg can also be a drug as described herein. In the structures shown above, the number of bonds between $R_3$ and $R_4$ are 3, 3, 4, and 6, respectively.

With S as a scaffold moiety, specific examples of $R_3-S-R_4$ include the following:

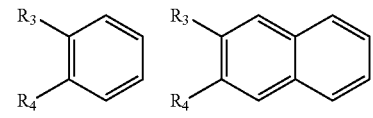

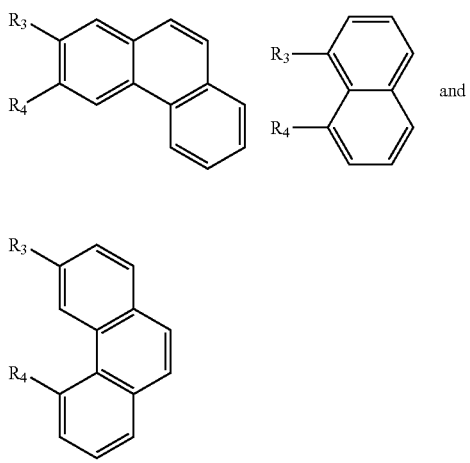

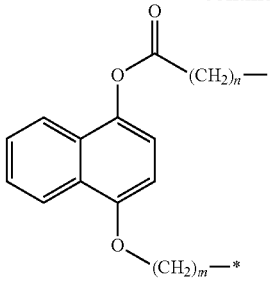

Combinations of bridge-induced turns and structural turns are also possible. For example, any of the scaffold moieties described herein can be used along with cysteines as R3 and R4 for formation of a disulfide bridge.

Further examples of R$_3$—S—R$_4$ include the following:

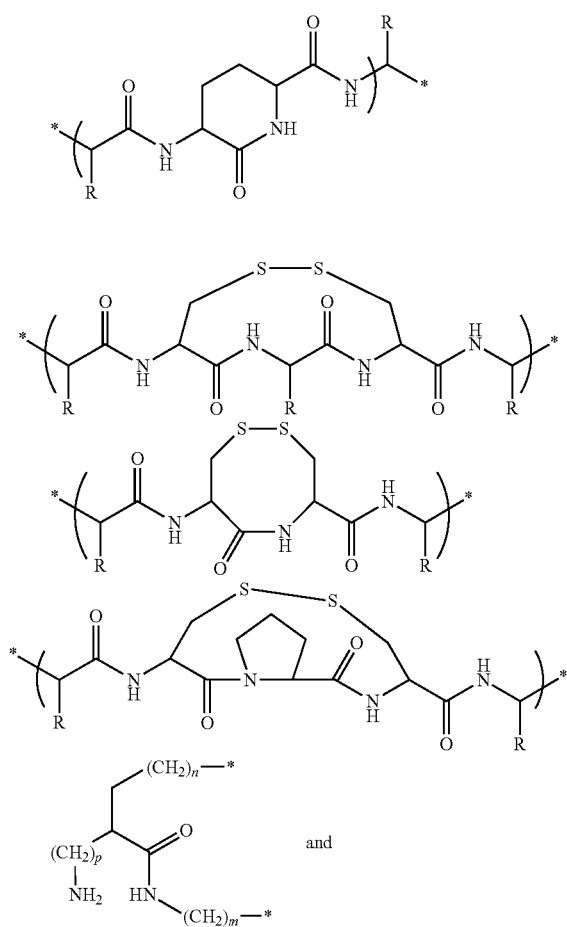

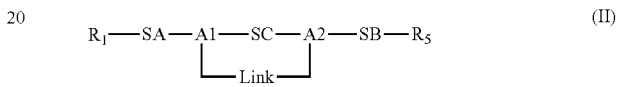

wherein m, n, and p are integers independently selected from 1, 2, 3, 4, and 5.

In some embodiments the inventive compounds have the structure of formula (II)

$$R_1\text{—SA—A1—SC—A2—SB—}R_5 \qquad (II)$$
$$\text{└—Link—┘}$$

wherein:
SA, SB, R$_1$, and R$_5$ are as described in formula (I);
SC is independently a linker selected from a bond, a peptide bond (i.e., a bond between two amino acids), an amino acid, a di-peptide and a tri-peptide;
A1 and A2 are amino acids;
Link is a bond between the side-chains of amino acids A1 and A2.

In some embodiments, A1 and A2 are selected from cysteine, serine, ornithine, and the like. In some embodiments, link is selected from an amide bond, a disulfide bond, an ether bond, a thioether bond, and the like.

In some embodiments the inventive compounds have the structure of formula (III)

wherein:
R$_1$, SA, SB, and R$_5$ are as defined for formula (II); and
Sca is a non-peptide chemical entity that connects SA to SB such that the shortest bond-path is n, where 2<n<10 bonds. For example, Sca can be any of the scaffold moieties described herein with respect to S.

A drug may be incorporated in the structure of formula (I). In some embodiments, the drug is incorporated into R$_1$, R$_5$, or S. By "incorporated into" is meant that the drug is covalently attached to one or more positions on the compound. For example, the drug may be attached at the N-terminus of R$_1$, or at the C-terminus of R$_5$. Alternatively, the drug may be attached to a branch point in S. Alternatively, the drug may be attached to a side chain in R$_3$, R$_4$, SA or SB.

Examples of drugs that may be incorporated into the inventive compounds include Aviptadil, Bivalirudin, Calcitonin (human), Calcitonin(salmon), Carperitide, Desmopressinm, Enfurivirtide, Eptifibatide, Exenatide, Lanreotide, liraglutide, Mifamurtide, Nesiritide, Pramlintide, Romiplostim, Taltirelin, and Teriparatide. Additional drugs include parathyroid hormone (PTH), and glucagon-like peptide-1 (GLP-1). Fragments (i.e., partial peptides) of any of these drugs may also be used, where such fragments are pharmaceutically active.

The inventive compounds selectively bind a serum albumin. By "selectively bind" is meant that the affinity of a compound for binding to a serum albumin is characterized by an equilibrium dissociation constant (Kd) that is less than about 1 µM, 750 nM, 500 nM, 250 nM, 100 nM, 50 nM, 10 nM, 1 nM, 500 pM, 250 pM, 100 pM, 50 pM, or 10 pM. In some embodiments, the compounds bind human serum albumin, a non-human serum albumin, or both human and non-human serum albumins. Examples of non-human serum albumin include bovine serum albumin, equine serum albumin, swine serum albumin, and the like.

In some embodiments, the inventive compounds include a second ligand that binds a circulating protein. In such embodiments, the compounds bind the circulating protein, as well as a serum albumin, as a double binding construct such as those described in detail in co-pending U.S. provisional patent application No. 61/651,513, entitled "Double Binding Constructs," filed May 24, 2012, concurrently with this application, the contents of which are incorporated herein by reference.

In particular, in some embodiments, the inventive compounds are double binding constructs. Such compounds bind serum albumin as described herein, and contain a second ligand that binds a second binding partner. The second binding partner can be a circulating protein (i.e., a plasma protein); examples include heat shock proteins (HSPs), Fc, ubiquitin, fibrinogens, immunoglobulins, $\alpha_1$-antitrypsin, $\alpha_2$-macroglobulins, transferrin, prothrombin, avidin, streptavidin, and the like. In some embodiments the second binding partner is a second serum albumin, such that the double binding construct binds two serum albumins.

In some embodiments of the double binding constructs, the construct incorporates a drug as described herein. In the free (i.e., unbound) construct, the drug is active (e.g., has an Kd value less than about 9, 8, 7, 6, 5, 4, 3, 2, 1.5, 1.25, or 1.1 times the Kd of the unincorporated parent drug). In the singly bound construct, the drug is also active (e.g., has an Kd value less than about 9, 8, 7, 6, 5, 4, 3, 2, 1.5, 1.25, or 1.1 times the Kd of the free construct). In the doubly bound construct, the drug is substantially de-activated (e.g., has an Kd value greater than about 10, 20, or 50 times the Kd of the unbound construct).

In some embodiments, the inventive compounds incorporate a drug, bind to a SA, and also incorporate a molecular weight increasing moiety. The molecular weight increasing moiety can be covalently bound to the compound through $R_1$, $R_5$, or S. Examples of molecular weight increasing moieties include large molecules such as proteins (e.g., HSA, etc.), polysaccharides (e.g., CMC, hyaluronic acid, etc.), synthetic polymers (e.g., PEG, polylactic acid, etc., including copolymers), glucoseaminoglycans (e.g., heparin), and the like. The molecular weight of suitable molecular weight increasing moieties may be greater than 5, 10, 15, 20, 25, 30, 35, 40, 45, or 50 kDa. For compounds incorporating a drug and a molecular weight increasing moiety, the free (i.e. unbound) compound is active (e.g., has an Kd value less than about 9, 8, 7, 6, 5, 4, 3, 2, 1.5, 1.25, or 1.1 times the Kd of the unincorporated parent drug), and the bound compound (i.e. bound to a SA) is substantially de-activated (e.g., has an Kd value greater than about 10, 20, or 50 times the Kd of the unbound construct).

Where an inventive compound includes a drug moiety, the compound has improved pharmacokinetics (PK) compared with the unincorporated parent drug. By "improved PK" is meant that at least one measure of PK is improved compared with the free drug. Examples of improved measures of PK include improved adsorption, improved distribution, reduced metabolism, reduced excretion, and reduced toxicity. For example, the compounds have a lower rate of kidney clearance, allowing the compounds to have an increased half-life.

The compounds in the form of double binding constructs have, for example, an improved therapeutic window, meaning that the compound can be administered at a higher dose (e.g., 2, 3, 4, 5, or more than 5 times the dose) compared with the unincorporated parent drug. The higher dose is possible because the compounds exhibit reduced toxicity (e.g., reduced liver toxicity) and have fewer side effects as a result of the inactivation of the doubly bound construct. Similarly, the compounds containing a molecular weight increasing moiety also have an improved therapeutic window.

Incorporating a drug into the inventive compounds is a method for altering the PK of the drug. The inventive compounds incorporating a drug can be used to treat a patient in need of treatment by the drug. Administration of the inventive compound to a patient in need thereof can be carried out at higher doses and less frequently (e.g., daily, or once every 2, 3, 4, 5, 6, or 7 days) compared with the unincorporated parent drug.

The inventive compounds can be prepared using any suitable method. The peptides described herein can be prepared using standard methods of peptide synthesis. A scaffold moiety can be synthesized using known methods of synthetic chemistry, and then incorporated into the inventive compounds. Similarly, drugs can be incorporated into the inventive compounds using either synthetic chemistry methods or peptide synthesis (e.g., gene expression).

Unless otherwise indicated, the disclosure is not limited to specific procedures, materials, or the like, as such may vary. It is also to be understood that the terminology used herein is for the purpose of describing particular embodiments only and is not intended to be limiting.

As used in the specification and the appended claims, the singular forms "a," "an," and the include plural referents unless the context clearly dictates otherwise. Thus, for example, reference to "a reactant" includes not only a single reactant but also a combination or mixture of two or more different reactant.

It is to be understood that while the invention has been described in conjunction with the preferred specific embodiments thereof, the description above as well as the examples that follow are intended to illustrate and not limit the scope of the invention. Other aspects, advantages and modifications within the scope of the invention will be apparent to those skilled in the art to which the invention pertains.

EXAMPLES

Example 1 hSA binding assay. Microtiter 96 well plate is coated, overnight at 4° C., using 150 ml per well of a solution of hSA in PBS (100 mg/ml). Plate is washed with PBS and blocked, for 1 hours, using 150 ml, per well, of a 10% solution of Tween 20 in water. After 1 hour the wells are washed with PBS. The hSA binders tested are dissolved in PBS, 100 ml of the tested solutions are then added in the well and incubated for 2 hours. After 2 hours, the solution are discarded and the wells are washed using PBS, 0.1% Tween 20. 100 ml of a solution of streptavidin-polyHRP in PBS 1.375% casein is added to the wells and incubated for 1 more hours. Finally wells are washed with PBS, 0.1% Tween 20, and 100 ml ABTS in phosphate-citrate buffer with sodium perborate is added. After a few minutes OD are read at 405 nm.

A plurality of compounds according to the invention were prepared. All of the compounds contained the Cys-Pro-Cys moiety. These compounds and an assay control were tested using the above procedure. Some compounds were tested twice (Exp 1 and Exp 2). Data are provided in Table 1.

TABLE 1

Binding of compounds

| | Compound[1] | SEQ ID NO: | Binding, Exp 1 | Binding, Exp 2 | $B_{max}$ |
|---|---|---|---|---|---|
| 1 | Assay Control | | 0.2089857 | 0.315 | 0.8157 |
| 2 | RQIEDI-LW | 7 | 0.0230588 | 0.2243 | 1.232 |
| 3 | KLISDI-LW | 8 | 0.0250389 | — | — |
| 4 | RLIADI-LW | 9 | 0.0347260 | 0.1216 | 1.036 |
| 5 | KLIEVI-LW | 10 | 0.0386750 | — | — |
| 6 | RLIDDI-LW | 11 | 0.0389676 | 0.2179 | 1.256 |
| 7 | RLTEDI-LW | 12 | 0.0390182 | — | — |
| 8 | RFIEDI-LW | 13 | 0.0414202 | 0.1971 | 1.136 |
| 9 | KLLEDI-LW | 14 | 0.0419715 | — | — |
| 10 | RLIEDI-FW | 15 | 0.0454368 | — | — |
| 11 | KLIEDE-LW | 16 | 0.0480808 | — | — |
| 12 | RLIVDI-LW | 17 | 0.0489471 | 0.2036 | 1.002 |
| 13 | KFIEDI-LW | 18 | 0.0497909 | 0.4961 | 1.198 |
| 14 | RLIENI-LW | 19 | 0.0533068 | — | — |
| 15 | KLIEDI-VW | 20 | 0.0554501 | — | — |
| 16 | RLIEDQ-LW | 21 | 0.0609237 | — | — |
| 17 | RLEEDI-LW | 22 | 0.0624988 | — | — |
| 18 | RLIQDI-LW | 23 | 0.0626113 | — | — |
| 19 | RVIEDI-LW | 24 | 0.0639052 | 0.2112 | 1.089 |
| 20 | RLVEDI-LW | 25 | 0.0640740 | — | — |
| 21 | KLIEDI-LK | 26 | 0.0694744 | — | — |
| 22 | KTIEDI-LW | 27 | 0.0694744 | 0.1476 | 1.427 |
| 23 | KLIEDI-LH | 28 | 0.0716121 | — | — |
| 24 | KLTEDI-LW | 29 | 0.0735247 | — | — |
| 25 | KLIEDI-AW | 30 | 0.0828067 | — | — |
| 26 | KLIEDI-LW | 31 | 0.0874196 | — | — |
| 27 | RLIEDT-LW | 32 | 0.0895573 | — | — |
| 28 | RLIEEI-LW | 33 | 0.0964203 | — | — |
| 29 | KLIYDI-LW | 34 | 0.1014270 | 0.09262 | 0.7912 |
| 30 | KLIEDI-FW | 35 | 0.1032834 | — | — |
| 31 | KLQEDI-LW | 36 | 0.1033396 | — | — |
| 32 | RLIEDI-TW | 37 | 0.1125654 | — | — |
| 33 | KLFEDI-LW | 38 | 0.1212849 | — | — |
| 34 | KLIDDI-LW | 39 | 0.1237038 | — | — |
| 35 | KLIEDI-TW | 40 | 0.1327045 | — | — |
| 36 | RLIKDI-LW | 41 | 0.1403552 | — | — |
| 37 | RLIEVI-LW | 42 | 0.1502560 | — | — |
| 38 | RLIEDA-LW | 43 | 0.1522249 | — | — |
| 39 | KLIEDA-LW | 44 | 0.1530124 | — | — |
| 40 | RIIEDI-LW | 45 | 0.1631945 | 0.1166 | 0.6826 |
| 41 | KLVEDI-LW | 46 | 0.1634758 | — | — |
| 42 | KLIEDI-LQ | 47 | 0.1651072 | — | — |
| 43 | RLIEDI-LV | 48 | 0.1700576 | — | — |
| 44 | KLIEDF-LW | 49 | 0.1836149 | — | — |
| 45 | Assay control | | 0.2089857 | 0.315 | 0.8157 |
| 46 | KLIADI-LW | 50 | 0.2126423 | 0.1074 | 1.077 |
| 47 | KQIEDI-LW | 51 | 0.2410508 | 0.581 | 1.4 |
| 48 | KLIEDI-QW | 52 | 0.2444824 | — | — |
| 49 | KLIEDI-LE | 53 | 0.2708658 | — | — |
| 50 | RLIEDI-LW | 54 | 0.2855482 | 0.3359 | 1.14 |
| 51 | KLIQDI-LW | 55 | 0.3066437 | 0.1771 | 1.048 |
| 52 | RLIEDI-VW | 56 | 0.3108065 | — | — |
| 53 | KLIEYI-LW | 57 | 0.3108628 | — | — |
| 54 | RLIEDV-LW | 58 | 0.3335896 | — | — |
| 55 | KLIEDQ-LW | 59 | 0.5208611 | — | — |
| 56 | KLIEDV-LW | 60 | 0.5310995 | — | — |
| 57 | RLIEEI-LW | 61 | 0.7026196 | — | — |
| 58 | RLIEDE-LW | 62 | 0.8196292 | — | — |
| 59 | RLIEDI-AW | 63 | 1.0311460 | — | — |
| 60 | RLIEDI-QW | 64 | 1.1931600 | — | — |
| 61 | RLIESI-LW | 65 | 1.2381630 | — | — |
| 62 | KIIEDI-LW | 66 | 1.4153650 | 0.2342 | 0.8075 |
| 63 | RLIEDI-LH | 67 | 1.8772150 | — | — |
| 64 | KVIEDI-LW | 68 | 2.5753340 | 0.1137 | 0.3906 |
| 65 | RLIEDI-LQ | 69 | 5.7885960 | — | — |
| 66 | RLIEDI-LK | 70 | 6.2273810 | — | — |
| 93 | KEIEDI-LW | 71 | — | 0.257 | 1.425 |
| 94 | LKIKDI-LW | 72 | — | 0.2987 | 1.253 |
| 95 | KLIVDI-LW | 73 | — | 0.1395 | 1.19 |
| 96 | REIEDI-LW | 74 | — | 0.2479 | 0.8746 |
| 97 | RLIQI-LW | 75 | — | 0.1909 | 0.8584 |

TABLE 1-continued

Binding of compounds

| | Compound[1] | SEQ ID NO: | Binding, Exp 1 | Binding, Exp 2 | $B_{max}$ |
|---|---|---|---|---|---|
| 98 | RLISDI-LW | 76 | — | 0.2247 | 1.301 |
| 99 | RTIEDI-LW | 77 | — | 0.1598 | 0.6151 |

[1]In thecompounds, "-" represents cysteine-proline-cysteine

Example 2

The compounds in Tables 2-5 are prepared:

TABLE 2

("Leu-Ile-Glu-Asp-Ile" disclosed as SEQ ID NO: 1)

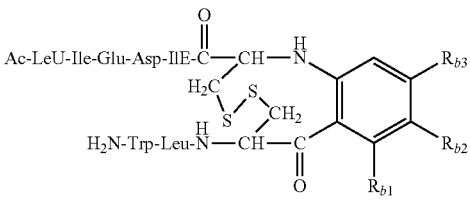

| Compound | $R_{b1}$ | $R_{b2}$ | $R_{b3}$ |
|---|---|---|---|
| 67 | Calcitonin | H | H |
| 68 | H | GLP-1 | H |
| 69 | H | H | Aviptadil |
| 70 | H | —CH=CH—CH=CH— | |
| 71 | H | H | H |
| 72 | —CH=CH—CH=CH— | | H |
| 73 | H | Me | H |
| 74 | H | H | OMe |

TABLE 3

("Leu—Ile—Glu—Asp—Ile" disclosed as SEQ ID NO: 1)

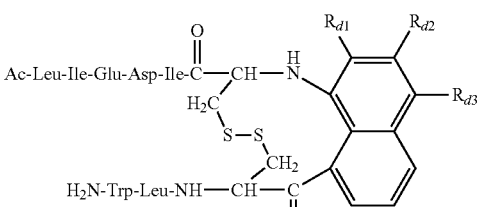

| Compound | $R_{d1}$ | $R_{d2}$ | $R_{d3}$ |
|---|---|---|---|
| 75 | Calcitonin | H | H |
| 76 | H | GLP-1 | H |
| 77 | H | H | Aviptadil |
| 78 | H | —CH=CH—CH=CH— | |
| 79 | H | H | H |
| 80 | —CH=CH—CH=CH— | | H |
| 81 | H | Me | H |
| 82 | H | H | OMe |

TABLE 4

("Leu—Ile—Glu—Asp—Ile" disclosed as SEQ ID NO: 1)

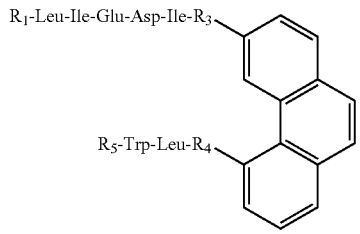

| Compound | $R_1$ | $R_3$ | $R_4$ | $R_5$ |
|---|---|---|---|---|
| 83 | Ac | Cys | Cys | $NH_2$ |
| 84 | Ac | -- | -- | $NH_2$ |
| 85 | Ac | $CH_2$ | $CH_2$ | GLP-1 |
| 86 | Calcitonin | Cys | Cys | $NH_2$ |
| 86 | Ac | -- | -- | Calcitonin |
| 87 | GLP-1 | $CH_2$ | $CH_2$ | $NH_2$ |
| 88 | Ac-Arg- | Cys | Cys | $NH_2$ |
| 89 | Ac-Lys | -- | -- | $NH_2$ |

"--" represents a direct bond

TABLE 5

("Leu—Ile—Glu—Asp—Ile" disclosed as SEQ ID NO: 1)

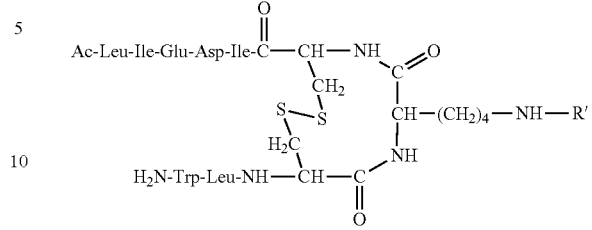

| Compound | R' |
|---|---|
| 90 | H |
| 91 | Calcitonin |
| 92 | GLP-1 |

Syntheses of compounds 91 and 92 are carried out by preparing compound 90, and then conjugating the compound to the appropriate drug. Alternatively, the appropriate drug is synthesized with a lysine residue at the terminus, which residue is then conjugated to the sequences LIEDIC (SEQ ID NO: 78) and WLC.

---

What is claimed is:

1. A compound of general formula (I):

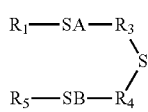

wherein:
SA is a pentapeptide aa1--aa2--aa3--aa4--aa5, wherein at least three of the following five requirements are satisfied: aa1 is L, aa2 is I, aa3 is E, aa4 is D, and aa5 is I, wherein L is Leu, I is Ile, E is Glu, and D is Asp;
SB is a dipeptide LW, wherein L is Leu and W is Trp;
$R_1$ is N—R, wherein N is amino and R is arginine or lysine, or $R_1$ is acyl; and $R_5$ is amide, a carboxylate group, or hydrogen;
$R_3$ and $R_4$ are cysteine residues; and
S is a peptide bond, an amino acid, or a peptide of up to three residues,
wherein $R_3$, S, and $R_4$ together form a turn in the compound, and the length of the turn formed by $R_3$, S, and $R_4$ is five peptide bonds or less.

2. The compound of claim , wherein SA is LIEDI (SEQ ID NO: 1).

3. The compound of claim 1, wherein $R_3$ and $R_4$ are cysteine residues that bind each other through disulfide binding.

4. The compound of claim I, wherein S is proline.

* * * * *

SEQUENCE LISTING

```
<160> NUMBER OF SEQ ID NOS: 78

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Ile Glu Asp Ile
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<223> OTHER INFORMATION: See specification as filed for detailed
      description of substitutions and preferred embodiments

<400> SEQUENCE: 2

Leu Ile Glu Asp Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
```

```
<223> OTHER INFORMATION: Any amino acid
<220> FEATURE:
<223> OTHER INFORMATION: See specification as filed for detailed
      description of substitutions and preferred embodiments

<400> SEQUENCE: 3

Leu Ile Glu Xaa Ile
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<223> OTHER INFORMATION: See specification as filed for detailed
      description of substitutions and preferred embodiments

<400> SEQUENCE: 4

Leu Ile Xaa Asp Ile
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<223> OTHER INFORMATION: See specification as filed for detailed
      description of substitutions and preferred embodiments

<400> SEQUENCE: 5

Leu Xaa Glu Asp Ile
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<223> OTHER INFORMATION: See specification as filed for detailed
      description of substitutions and preferred embodiments

<400> SEQUENCE: 6

Xaa Ile Glu Asp Ile
1               5

<210> SEQ ID NO 7
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 7

Arg Gln Ile Glu Asp Ile Cys Pro Cys Leu Trp
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Leu Ile Ser Asp Ile Cys Pro Cys Leu Trp
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Leu Ile Ala Asp Ile Cys Pro Cys Leu Trp
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Leu Ile Glu Val Ile Cys Pro Cys Leu Trp
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Leu Ile Asp Asp Ile Cys Pro Cys Leu Trp
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Leu Thr Glu Asp Ile Cys Pro Cys Leu Trp
1               5                   10
```

```
<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Phe Ile Glu Asp Ile Cys Pro Cys Leu Trp
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Leu Leu Glu Asp Ile Cys Pro Cys Leu Trp
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Leu Ile Glu Asp Ile Cys Pro Cys Phe Trp
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Leu Ile Glu Asp Glu Cys Pro Cys Leu Trp
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Leu Ile Val Asp Ile Cys Pro Cys Leu Trp
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Lys Phe Ile Glu Asp Ile Cys Pro Cys Leu Trp
1               5                   10
```

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Arg Leu Ile Glu Asn Ile Cys Pro Cys Leu Trp
1               5                   10
```

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Lys Leu Ile Glu Asp Ile Cys Pro Cys Val Trp
1               5                   10
```

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Arg Leu Ile Glu Asp Gln Cys Pro Cys Leu Trp
1               5                   10
```

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Arg Leu Glu Glu Asp Ile Cys Pro Cys Leu Trp
1               5                   10
```

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Arg Leu Ile Gln Asp Ile Cys Pro Cys Leu Trp
1               5                   10
```

<210> SEQ ID NO 24
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 24

Arg Val Ile Glu Asp Ile Cys Pro Cys Leu Trp
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Leu Val Glu Asp Ile Cys Pro Cys Leu Trp
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Leu Ile Glu Asp Ile Cys Pro Cys Leu Lys
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Thr Ile Glu Asp Ile Cys Pro Cys Leu Trp
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Leu Ile Glu Asp Ile Cys Pro Cys Leu His
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Leu Thr Glu Asp Ile Cys Pro Cys Leu Trp
1               5                   10
```

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Leu Ile Glu Asp Ile Cys Pro Cys Ala Trp
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Leu Ile Glu Asp Ile Cys Pro Cys Leu Trp
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Leu Ile Glu Asp Thr Cys Pro Cys Leu Trp
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Leu Ile Glu Glu Ile Cys Pro Cys Leu Trp
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Leu Ile Tyr Asp Ile Cys Pro Cys Leu Trp
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 35

Lys Leu Ile Glu Asp Ile Cys Pro Cys Phe Trp
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Leu Gln Glu Asp Ile Cys Pro Cys Leu Trp
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Leu Ile Glu Asp Ile Cys Pro Cys Thr Trp
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Leu Phe Glu Asp Ile Cys Pro Cys Leu Trp
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Leu Ile Asp Asp Ile Cys Pro Cys Leu Trp
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Leu Ile Glu Asp Ile Cys Pro Cys Thr Trp
1               5                   10

<210> SEQ ID NO 41
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 41

Arg Leu Ile Lys Asp Ile Cys Pro Cys Leu Trp
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Leu Ile Glu Val Ile Cys Pro Cys Leu Trp
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Leu Ile Glu Asp Ala Cys Pro Cys Leu Trp
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Leu Ile Glu Asp Ala Cys Pro Cys Leu Trp
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ile Ile Glu Asp Ile Cys Pro Cys Leu Trp
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Leu Val Glu Asp Ile Cys Pro Cys Leu Trp
1               5                   10
```

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Leu Ile Glu Asp Ile Cys Pro Cys Leu Gln
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Leu Ile Glu Asp Ile Cys Pro Cys Leu Val
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Leu Ile Glu Asp Phe Cys Pro Cys Leu Trp
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Leu Ile Ala Asp Ile Cys Pro Cys Leu Trp
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Gln Ile Glu Asp Ile Cys Pro Cys Leu Trp
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Leu Ile Glu Asp Ile Cys Pro Cys Gln Trp
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Leu Ile Glu Asp Ile Cys Pro Cys Leu Glu
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Leu Ile Glu Asp Ile Cys Pro Cys Leu Trp
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Leu Ile Gln Asp Ile Cys Pro Cys Leu Trp
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Leu Ile Glu Asp Ile Cys Pro Cys Val Trp
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Leu Ile Glu Tyr Ile Cys Pro Cys Leu Trp
1               5                   10

<210> SEQ ID NO 58
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Leu Ile Glu Asp Val Cys Pro Cys Leu Trp
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Leu Ile Glu Asp Gln Cys Pro Cys Leu Trp
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Leu Ile Glu Asp Val Cys Pro Cys Leu Trp
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Leu Ile Glu Glu Ile Cys Pro Cys Leu Trp
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Leu Ile Glu Asp Glu Cys Pro Cys Leu Trp
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Leu Ile Glu Asp Ile Cys Pro Cys Ala Trp
```

-continued

```
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Leu Ile Glu Asp Ile Cys Pro Cys Gln Trp
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Leu Ile Glu Ser Ile Cys Pro Cys Leu Trp
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Ile Ile Glu Asp Ile Cys Pro Cys Leu Trp
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Leu Ile Glu Asp Ile Cys Pro Cys Leu His
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Val Ile Glu Asp Ile Cys Pro Cys Leu Trp
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 69

Arg Leu Ile Glu Asp Ile Cys Pro Cys Leu Gln
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Leu Ile Glu Asp Ile Cys Pro Cys Leu Lys
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Glu Ile Glu Asp Ile Cys Pro Cys Leu Trp
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Lys Ile Lys Asp Ile Cys Pro Cys Leu Trp
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Leu Ile Val Asp Ile Cys Pro Cys Leu Trp
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Glu Ile Glu Asp Ile Cys Pro Cys Leu Trp
1               5                   10

<210> SEQ ID NO 75

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Leu Ile Gln Ile Cys Pro Cys Leu Trp
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Leu Ile Ser Asp Ile Cys Pro Cys Leu Trp
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Thr Ile Glu Asp Ile Cys Pro Cys Leu Trp
1               5                   10

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Ile Glu Asp Ile Cys
1               5
```